US008791428B2

(12) United States Patent
Lau et al.

(10) Patent No.: US 8,791,428 B2
(45) Date of Patent: Jul. 29, 2014

(54) AUTHENTICATION SYSTEMS FOR DISCRIMINATING VALUE DOCUMENTS BASED ON VARIABLE LUMINESCENCE AND MAGNETIC PROPERTIES

(75) Inventors: Carsten Lau, Niedersachsen (DE); James Kane, Lawrenceville, NJ (US); William Ross Rapoport, Bridgewater, NJ (US)

(73) Assignee: Honeywell International Inc., Morristown, NJ (US)

( * ) Notice: Subject to any disclaimer, the term of this patent is extended or adjusted under 35 U.S.C. 154(b) by 700 days.

(21) Appl. No.: 12/893,106

(22) Filed: Sep. 29, 2010

(65) Prior Publication Data
US 2011/0087440 A1    Apr. 14, 2011

Related U.S. Application Data

(60) Provisional application No. 61/251,503, filed on Oct. 14, 2009.

(51) Int. Cl.
| | |
|---|---|
| *G07D 7/04* | (2006.01) |
| *G07D 7/12* | (2006.01) |
| *G01N 21/64* | (2006.01) |
| *G01R 23/16* | (2006.01) |
| *G06K 9/78* | (2006.01) |
| *G06K 7/01* | (2006.01) |

(52) U.S. Cl.
CPC ............... *G07D 7/04* (2013.01); *G07D 7/122* (2013.01); *G07D 7/124* (2013.01); *G01N 21/64* (2013.01); *G01R 23/16* (2013.01); *G06K 9/78* (2013.01); *G06K 7/01* (2013.01)
USPC ...................................................... 250/458.1

(58) Field of Classification Search
CPC ........... G01K 7/01; G06K 8/78; G01R 23/16; G01N 23/64; G07D 7/04; G07D 7/122; G07D 7/124

USPC .......................................... 250/458.1–461.1
See application file for complete search history.

(56) References Cited

U.S. PATENT DOCUMENTS 3,612,835 A * 10/1971 Andrews et al. ............. 235/440
4,146,792 A *  3/1979 Stenzel et al. ................ 250/365
(Continued)

FOREIGN PATENT DOCUMENTS

| CN | 2667578 Y | 12/2004 |
|---|---|---|
| CN | 1601565 A | 3/2005 |
| JP | 2004185126 A * | 7/2004 |

OTHER PUBLICATIONS

Korean Intellectual Property Office, International Searching Authority, "International Search Report" mailed Jun. 1, 2011; International Appln. No. PCT/US2010/050872, filed Sep. 30, 2010.

*Primary Examiner* — Casey Bryant
(74) *Attorney, Agent, or Firm* — Ingrassia Fisher & Lorenz PC

(57) ABSTRACT

A value document authentication system comprising a value document substrate having a luminescent compound disposed on or in at least a portion of the value document substrate, wherein the luminescent compound (i) comprises a host lattice having at least one metallic ion with magnetic properties and is doped with at least one rare earth ion capable of emitting infrared radiation with at least one distinct infrared wavelength when excited with an exciting light source having sufficient energy to excite emission from the luminescent compound and (ii) has a pre-determined ratio of metallic ions to rare earth ions such that the ratio corresponds to a parameter of a pre-selected decision criteria, both of which properties are measured at the same location on the value document and used to authenticate the value document.

19 Claims, 1 Drawing Sheet

(56) References Cited

U.S. PATENT DOCUMENTS

| | | | |
|---|---|---|---|
| 4,446,204 A * | 5/1984 | Kaule et al. | 428/323 |
| 6,344,261 B1 * | 2/2002 | Kaule et al. | 428/195.1 |
| 2004/0094723 A1 | 5/2004 | Walker | |
| 2008/0005037 A1 | 1/2008 | Hammad et al. | |
| 2009/0051158 A1 | 2/2009 | Scholz et al. | |
| 2010/0261211 A1 | 10/2010 | Ataullakhanov et al. | |
| 2011/0069174 A1 * | 3/2011 | Rapoport et al. | 348/161 |
| 2011/0121203 A1 * | 5/2011 | Rapoport et al. | 250/459.1 |
| 2011/0146930 A1 * | 6/2011 | Kane et al. | 162/181.1 |
| 2011/0147450 A1 * | 6/2011 | Rapoport et al. | 235/375 |
| 2011/0147614 A1 * | 6/2011 | Kane et al. | 250/459.1 |
| 2012/0104256 A1 * | 5/2012 | Rapoport et al. | 250/340 |
| 2012/0153184 A1 * | 6/2012 | Kane | 250/458.1 |

* cited by examiner

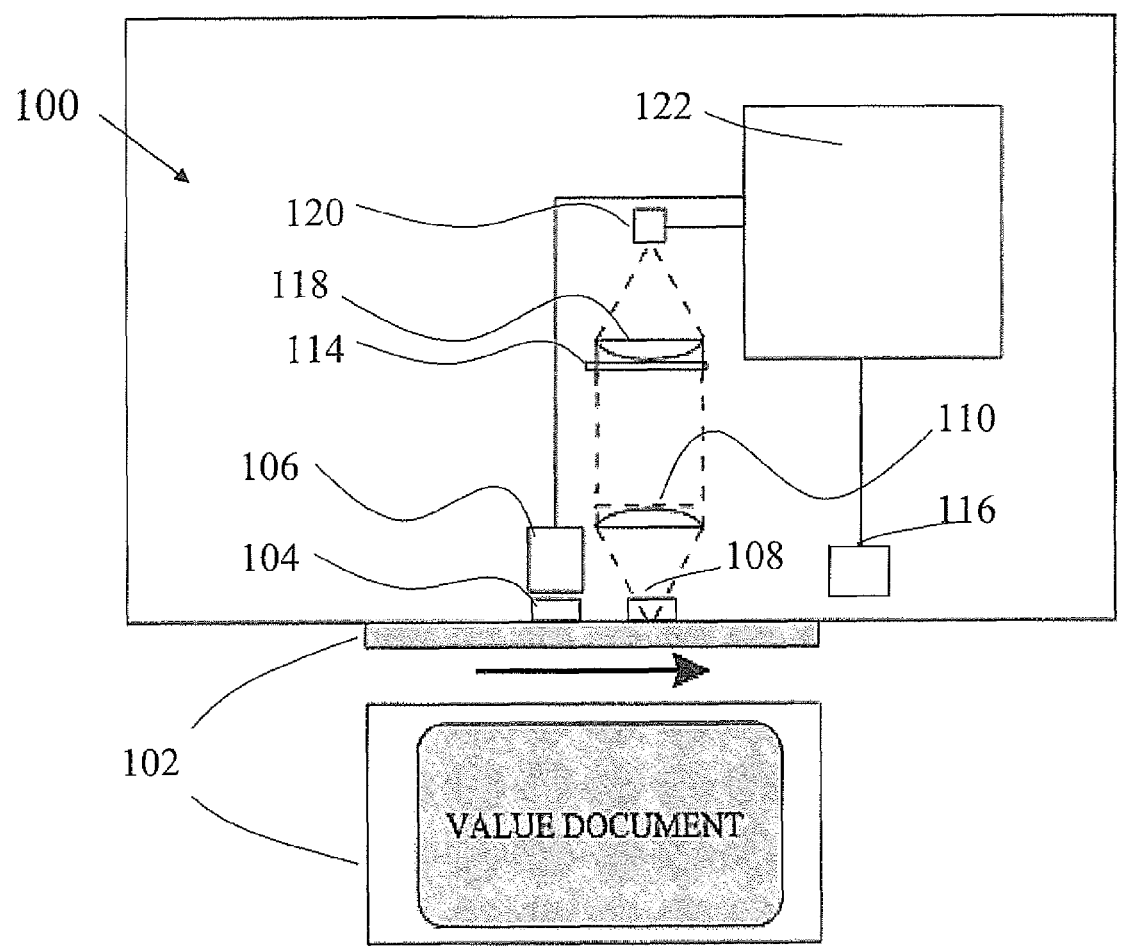

AUTHENTICATION SYSTEMS FOR DISCRIMINATING VALUE DOCUMENTS BASED ON VARIABLE LUMINESCENCE AND MAGNETIC PROPERTIES

CROSS-REFERENCES TO RELATED APPLICATIONS

This application claims the benefit of U.S. Provisional application No. 61/251,503 filed Oct. 14, 2009.

FIELD OF THE INVENTION

This invention relates to systems for detecting and authenticating value documents having variable luminescent and magnetic properties.

DESCRIPTION OF RELATED ART

In many applications, it is necessary to distinguish an original article and/or document from a copy or counterfeit. With modern copying techniques, for instance, printed material can be reproduced easily and can be virtually indistinguishable from the original. Various means and methods have been used for marking and identifying original items. For example, some methods involve visible (i.e. overt) features on or incorporated into a document, such as a hologram on a credit card, an embossed image or watermark on a bank note, a security foil, a security ribbon, colored threads or colored fibers within a bank note, or a floating and/or sinking image on a passport. While these features are easy to detect with the eye and may not require equipment for authentication, these overt features are easily identified by a would-be forger and/or counterfeiter. As such, in addition to overt features, hidden (i.e. covert) features may be incorporated into an article. Covert features include invisible fluorescent fibers, chemically sensitive stains, fluorescent pigments or dyes that are incorporated into the substrate of the value document. Covert features may also be included in the ink that is printed onto the substrate of an item or within the resin used to make films that are used to make laminated products. Since covert features are not detectable by the human eye, detectors configured to detect these covert features are needed to authenticate the article, which increases its security and helps mitigate against forgery or falsification.

There have been efforts to combine authenticatable features, mask covert features or otherwise render security features more difficult to detect. For example, U.S. Pat. No. 4,446,204 (Kaule) discloses a security paper that is marked with authenticable features in the form of coloring agents that have IR-transmission properties and magnetic properties, wherein both IR transmission and magnetic tests can be uninfluenced by one another but are capable of being carried out at the same position on the security paper. Known detection devices are then used to match detectors to the differently lying spectral region of the authenticable features for validation. U.S. Pat. No. 5,569,317 (Sarada) discloses the use of an ink having not only fluorescent emissions, but also covert phosphorescent emissions. U.S. Pat. No. 4,500,116 (Ferro) describes marking a credential, such as a passport or an identification card by impregnation or coating the credential with a phosphorescent composition which includes at least two phosphorescence activators which exhibit different emission characteristics both with respect to wavelength and lifetime. For example, when the article is illuminated, the afterglow color changes from green to blue. In U.S. Pat. Application Publication No. 2007/0295116, a process for authenticating articles is described that uses a phosphor to produce two different wavelength emissions, each having different decay times. Other examples of mixed phosphors for authentication purposes having different excitation and emissions wavelengths are disclosed in U.S. Pat. No. 4,387,112.

While pigments producing multiple luminescent emissions thwart inexperienced forgers and/or counterfeiters, those who are sophisticated and have the resources may be able to reproduce such covert features. This is particularly true for articles incorporating well known luminescent compositions whose properties, such as excitation wavelength and emission wavelengths, are published. Even proprietary luminescent compositions are subject to detection and reverse engineering by counterfeiters. Therefore, there remains a need for methods of authenticating articles and authentication systems that incorporate covert features in and/or on the article that are difficult to replicate and have a detection system that is complicated enough to prevent counterfeiting and forging of the article.

SUMMARY OF THE INVENTION

This invention relates to an authentication system for discriminating a value document, including a. a value document substrate; b. a luminescent compound disposed on or in at least a portion of the value document substrate, wherein the luminescent compound (i) comprises a host lattice having at least one metallic ion with magnetic properties and is doped with at least one rare earth ion capable of emitting infrared radiation when excited with an exciting light source and (ii) has a pre-determined ratio of metallic ions to rare earth ions such that the ratio corresponds to a parameter of a pre-selected decision criteria; c. at least one optical sensor arranged to detect, with spectral resolution, infrared radiation emitted from the luminescent compound excited by the exciting light source and to produce intensity data; d. at least one magnetic sensor arranged to detect magnetic properties of the luminescent compound and to produce magnetic data; and e. a processing unit operating under a predefined program wherein the processing unit correlates the intensity data and the magnetic data for the value document, compares the intensity data with previously stored reference intensity data and the magnetic data with previously stored reference magnetic data, derives an authenticity indicator from the comparison using the pre-selected decision criteria, and communicates the authenticity indicator thereby indicating authentication or lack of authentication of the value document.

This invention relates to a method of securing a value document involving the step of pre-determining a ratio of metallic ions to rare earth ions such that the ratio corresponds to a parameter of a pre-selected authentication criteria, providing a luminescent compound comprising a host lattice having at least one metallic ion with magnetic properties and at least one rare earth ion capable of emitting infrared radiation when excited with an exciting light source and having the ratio, and adding the luminescent compound to the value document. The method further involving the steps of detecting magnetic data and intensity data, correlating the intensity data and the magnetic data, comparing the intensity data with previously stored reference intensity data and the magnetic data with previously stored reference magnetic data, and authenticating the value document based on the pre-selected authentication criteria.

BRIEF DESCRIPTION OF THE DRAWINGS

The invention will be more fully understood and further advantages will become apparent when reference is made to the following detailed description of the preferred embodiments of the invention and the accompanying drawing, in which:

FIG. 1 illustrates a schematic diagram of the authentication system wherein a value document is moved under an exciting light source and the emitted infrared radiation from the luminescent composition in or on the value document substrate is measured by an optical sensor at one or more wavelengths and is moved under a magnetic sensor and the magnetic properties of the luminescent composition are measured.

DETAILED DESCRIPTION OF THE INVENTION

Articles, such as value documents, may be designed with one or more covert authenticatable feature on or incorporated into the substrate of the value document in addition to the overt features that make it recognizable by the general public. Covert features include, but are not limited to, microprinting, multiple inks, UV absorbing visible emitting materials, upconverters, complex printing profiles, clear inks, infrared absorbing materials, magnetic inks, phosphors and varnishes. Over time, the use of covert features has become less secure since counterfeiters have become more sophisticated and have greater access to scientific equipment that can detect the incorporation of these features in value documents.

One possible method of improving the security of an article is to use authenticatable features, such as luminescent compositions, that are hard to manufacture and/or are difficult to identify within the document. Another possible method is to increase the intelligence of a detector, so that rather than having the pass/fail parameter depend on simply detecting the presence of the authenticatable feature alone, the detector may be configured to, for instance, detect in pre-selected regions of emission spectra, or be dependent upon amounts of the authenticatable feature, or dependent upon interactions between authenticatable features. Further yet, by using materials that are difficult to make and/or that exhibit spectral and temporal characteristics that are very difficult to mimic, combined with a smart detector, the security of an article may be enhanced.

The present invention relates to an authentication system comprising a luminescent compound disposed on or in at least a portion of the value document substrate, wherein the luminescent compound comprises a host lattice having at least one metallic ion with magnetic properties and is doped with at least one rare earth ion capable of emitting infrared radiation with at least one distinct infrared wavelength when excited with a exciting light source having sufficient energy to excite emission from the compound. The luminescent compound also has a pre-determined ratio of metallic ions to rare earth ions such that the ratio corresponds to at least one detection parameter for the authentication or rejection of a value document. By controlling this ratio within a single compound, the magnetic and luminescent responses of the luminescent compound may be tailored to provide unique detection parameters used for authentication.

Host materials of the present invention include garnets, perovskites, ilmenites, magnetoplumbites, ferrites, spinels, and derivatives thereof. Such host materials may be ferromagnetic, ferrimagnetic, or paramagnetic. For instance, it is well known that yttrium iron garnet (YIG) is a highly magnetic material. Preferably, the host material has a garnet structure described by the following general formula:

$$A_3B_{5-x}C_xO_{12}$$

where A stands for at least one ion from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, and sodium and combinations thereof; B stands for at least one ion from the elements selected from the group consisting of iron, nickel, cobalt, chromium, manganese, vanadium and combinations thereof; C stands for at least one diamagnetic ion from the elements selected from the group consisting of aluminum, bismuth, gallium, scandium, chromium, titanium, germanium, vanadium, zinc, zirconium, magnesium, silicon and combinations thereof; and x fulfills the condition $0 \leq x < 5$. Component A may comprise at least two, three, four or more ions from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, and sodium. Component B may comprise at least two or more ions from the elements selected from the group consisting of iron, nickel, cobalt, chromium, manganese, and vanadium. Component C may comprise at least two ions from the elements selected from the group consisting of aluminum, bismuth, gallium, scandium, chromium, titanium, germanium, vanadium, zinc, zirconium, magnesium, and silicon. In a preferred embodiment, Component A is selected from yttrium, lutetium, gadolinium and mixtures thereof, Component B is iron, and Component C is selected from aluminum, gallium, scandium, and mixtures thereof. The iron or chromium of the host lattice of the present invention may also be used as absorptive elements.

In terms of the composition $A_3B_{5-x}C_xO_{12}$, Component A may be selected to contribute to the luminescent effect via absorption, energy transfer, and/or IR emission and may contribute to the magnetic effect by comprising paramagnetic ions, such as lanthanide ions with unpaired electrons. Component B may also be selected to contribute to the luminescent effect via absorption, energy transfer, and/or in some cases IR emission (e.g. Cr) and may contribute to the magnetic effect by varying the amount of metallic ions with magnetic properties. Component C may be used to alter the content of metallic ions to vary the overall magnetic properties of the luminescent compound of the present invention, since the presence of Component C means the loss of Component B.

The luminescent compound of the present invention has the following general formula:

$$A_{3-y}RE_yB_{5-x}C_xO_{12}$$

where A stands for at least one ion from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, sodium and combinations thereof RE stands for at least one ion from the elements selected from the group consisting of praseodymium, neodymium, samarium, dysprosium, holmium, erbium, thulium, ytterbium, and combinations thereof B stands for at least one ion from the elements selected from the group consisting of iron, nickel, cobalt, chromium, manganese, vanadium and combinations thereof C stands for at least one diamagnetic ion from the elements selected from the group consisting of aluminum, bismuth, gallium, scandium, chromium, titanium, germanium, vanadium, zinc, zirconium, magnesium, silicon and combinations thereof x fulfills the condition $0 \leq x < 5$, and y fulfills the condition $0.001 \leq y < 3$. Component RE may comprise at least two ions from the elements selected from the group consisting of praseodymium, neodymium, samarium, dysprosium, holmium, erbium, thulium, and ytterbium. Preferably, Component RE is pre-selected to be excited by ultraviolet (UV), visible, or IR radiation, with IR radiation being preferred. After being excited by radiation, preferred Component RE ions produce at least one radiant emission in the infrared (IR) spectrum—i.e., at wavelengths between about 700 nm and about 3000 nm. Preferred Component RE ions of the present invention include ions from the elements selected from thulium, holmium, erbium, and mixtures thereof. Component RE ions may be selected to have magnetic moments that impact the overall magnetism of the luminescent compound. Component RE ions may also be selected to have optical properties that impact the overall luminescence of the luminescent compound.

Depending on the desired results, the magnetism of a luminescent composition may be altered to impact its luminescent characteristics as well. In the present invention, it has been determined that the magnetism of YIG may be altered by exchanging the iron ions of the crystal structure with, for instance, aluminum, gallium, or scandium ions, while not necessarily altering its optical characteristic and by doing so, create unique detection parameters based on, for instance, emissions, magnetism, absorption, decay times, and the like which may be pre-selected and used as authentication parameters. For instance, if the iron content of YIG is significantly reduced (e.g. to only 10%), the magnetic properties will be detectably altered and the luminescence will also be reduced since iron content is needed for absorption, which in turn impacts luminescence. The exchanging of ions is commonly practiced by those in the art by known methods.

While not being bound to any theory, it is believed that since iron ions occupy two different sites within the host lattice of YIG, the ferrimagnetism of YIG results from the magnetic moments of each iron ion in the two different sublattices. Specifically, per formula unit $Y_3Fe_5O_{12}$, three iron ions occupy tetrahedral sites ($Fe_{tet}$), and two iron ions occupy octahedral sites ($Fe_{oct}$). It is believed that the resulting magnetic moment of YIG is 3×5 BM ($Fe_{tet}$)–2×5 BM ($Fe_{oct}$)=5 BM per formula unit $Y_3(Fe_2)_{oct}(Fe_3)_{tet}O_{12}$. By exchanging some of the $Fe_{oct}$ sublattice ions with non-magnetic (diamagnetic) ions, the magnetic moment increase as follows: $Y_3(Fe_{1.75}Sc_{0.25})_{oct}(Fe_3)_{tet}O_{12}$ gives a magnetic moment of 3×5 BM ($Fe_{tet}$)–(2–0.25)×5 BM ($Fe_{oct}$)=6.25 BM per formula unit $Y_3(Fe_{1.75}Sc_{0.25})_{oct}(Fe_3)_{tet}O_{12}$. By exchanging some of the $Fe_{tet}$ sublattice ions with non-magnetic (diamagnetic) ions, the magnetic moment decreases as follows: $Y_3(Fe_2)_{oct}(Fe_{2.75}Ga_{0.25})_{tet}O_{12}$ gives a magnetic moment of (3–0.25)×5 BM ($Fe_{tet}$)–2×5 BM ($Fe_{oct}$)=3.75 BM per formula unit $Y_3(Fe_2)_{oct}(Fe_{2.75}Ga_{0.25})_{tet}O_{12}$. Changing the iron ion content by a small amount, e.g. 5%, shows a strong influence on the magnetic properties of the composition, whereas the optical properties remain nearly unaffected.

Another way of changing the magnetic properties independently from the luminescent properties may occur by changing the large cation Component A in the general formula $A_3B_{5-x}C_xO_{12}$. In YIG, $Y_3Fe_5O_{12}$, the A positions in the structure are all occupied by yttrium ions that do not have unpaired electrons and thus no magnetic moment. That is, all the magnetic moment of the compound is resulting from the iron ions as explained above and results as 5 BM. By putting ions with unpaired electrons in place, such as gadolinium ions with 7 unpaired electrons and hence an magnetic moment of 7 BM, the resulting overall magnetic moment for GIG, $Gd_3Fe_5O_{12}$, is given by 3×7–5=16 BM per formula unit. Changing the non-coloring yttrium ions with non-coloring gadolinium ions will not (or slightly if at all) affect the optical properties of the host, but results in up to about a threefold increase in magnetism.

According to the present invention, the authenticity of a value document is determined by a comparison of intensity data and magnetic data to pre-determined reference luminescent intensity data and magnetic data. These properties may be evaluated to the same time and place or may be evaluated at different times depending upon the system. The authentication system of the present invention involves at least one optical sensor arranged to detect, with spectral resolution, infrared radiation emitted from the luminescent compound excited by an exciting light source to produce intensity data. Suitable optical sensors include, for example, silicon, InGaAs, PbS, Ge and others that have the required spectral response, acceptable noise parameters, bandwidth and/or shunt impedance in the spectral detection regions as determined by one skilled in the art. These sensors produce signals that may be amplified by low noise electronics to a sufficient level such that they can be converted to digital values for processing. The output from the optical sensor depicts the intensity data of the infrared radiation. The authentication system of the present invention also has at least one magnetic sensor arranged to detect magnetic properties of the luminescent compound to produce magnetic data. Suitable magnetic sensors include any magnetometer or other device that has the required magnetic responses as determined by one skilled in the art.

The one or more processing units, such as a computer, may be used to store the reference data and collect, correlate, and discriminate test data. For instance, the one or more processing unit of the present invention operates under a predefined program wherein the processing unit correlates the test optical signals with the test magnetic data of a single value document, compares the test optical signals with previously stored reference optical signals, compares the test magnetic data with previously stored reference magnetic data and derives an authenticity indicator from the comparison results using a pre-selected decision criterion. The output unit, which may or may not be part of the processing unit, then communicates the authenticity indicator so as to indicate authentication or lack of authentication of the test value document.

According to the present invention, the luminescent compound may be applied to or incorporated within a value document substrate made of any material. Preferably, the value document substrate is a solid material, such as paper, film, plastic sheet, board, glass, textiles, fibers, and the like which may be subsequently used to produce value documents such as bank notes, checks, stamps, identity papers, passport, credit or bank card as well as labels, seals, packaging and other elements for product security. In one embodiment of the invention, the luminescent compound may be added to the paper pulp or plastic base resin material. The base material may take the form of a safety thread, a mottling thread, a planchet, a laminated film, a label. The luminescent compound may be incorporated into fibers or microfibers (made of different materials such as viscose or plastics). In still other embodiments, the luminescent compound may also be incorporated in a liquid carrier such as a printing ink that may be affixed to an article as a predetermined image or pattern, for example by coating or printing an image onto the value document.

The amount of luminescent composition in the authenticable feature may vary over a wide range. For example, the amount, expressed as weight of luminescent composition relative to the weight of substrate, may be between 0.001% and 20%, more particularly between 0.01% and 10% and even more particularly between 0.05% and 5%.

FIG. 1 illustrates a schematic diagram of the authentication apparatus 100. A value document 102 passes beneath the apparatus 100 moving first by an excitation window 104, having an exciting light source 106, wherein exciting light passes through the excitation window 104 to excite the luminescent composition contained in or on the value document 102. The value document 102 then passes beneath a detection window 108 wherein an infrared emission detector element 120 detects an infrared emission from the moving value document 102 as the emission passes up through the detection window 108. The infrared light signal is roughly collimated by lens 110, passed a first infrared filter 114, which is then focused by lens 118 onto detector element 120. The value document 102 then passes beneath a magnetic detector 116. A CPU 122 collects the signals from detector element 120 generating intensity data and detector element 116 generating magnetic data and, under a predefined program, correlates the intensity data and the magnetic data for the value document 102, compares the intensity data with previously stored reference intensity data and the magnetic data with previously stored reference magnetic data, derives an authenticity indicator from the comparison using the pre-selected decision criteria, and communicates the authenticity indicator thereby indicating authentication or lack of authentication of the value document.

Having thus described the invention in rather full detail, it will be understood that such detail need not be strictly adhered to, but that additional changes and modifications may suggest themselves to one skilled in the art, all falling within the scope of the invention as defined by the subjoined claims.

EXAMPLES

The following examples are provided to illustrate certain aspects of the invention. These examples are not to be construed as limiting the invention in any way.

Example 1

To yield $Y_{2.82}Er_{0.18}Fe_4AlO_{12}$, $Y_2O_3$ (22.01 g), $Er_2O_3$ (2.38 g), $Fe_2O_3$ (22.08 g), $Al_2O_3$ (3.52 g) and $Na_2SO_4$ (50 g) are intimately blended, added to an alumina crucible and fired for 12 hours at 1100° C. After cooling the reaction mixture, the product is suspended in water. Next, the fluxing agent is removed and the resulting product is dried at 120° C. in air. To achieve finer grain size, the material is then milled in a ball mill.

Example 2

To yield $Y_{1.41}Gd_{1.41}Er_{0.18}Fe_4AlO_{12}$, $Y_2O_3$ (9.71 g), $Gd_2O_3$ (15.59 g), $Er_2O$ (2.10 g), $Fe_2O_3$ (19.49 g), $Al_2O_3$ (3.11 g) and $Na_2SO_4$ (50 g) are intimately blended, added to an alumina crucible and fired for 12 hours at 1100° C. After cooling the reaction mixture, the product is suspended in water. Next, the fluxing agent is washed out and the resulting product is dried at 120° C. in air. To achieve finer grain size, the material is then milled in a ball mill.

Example 3

To yield $Gd_{2.82}Er_{0.18}Fe_4AlO_{12}$, $Gd_2O_3$ (27.90 g), $Er_2O_3$ (1.88 g), $Fe_2O_3$ (17.44 g), $Al_2O_3$ (2.78 g) and $Na_2SO_4$ (50 g) are intimately blended, added to an alumina crucible and fired for 12 hours at 1100° C. After cooling the reaction mixture, the product is suspended in water. Next, the fluxing agent is washed out and the resulting product is dried at 120° C. in air. To achieve finer grain size, the material is then milled in a ball mill.

What is claimed is:

1. An authentication system for discriminating a value document, comprising:
    a) a value document substrate;
    b) a luminescent compound disposed on or in at least a portion of the value document substrate, wherein the luminescent compound (i) comprises a host lattice having at least one metallic ion with magnetic properties and is doped with at least one rare earth ion capable of emitting infrared radiation when excited with an exciting light source and (ii) has a pre-determined ratio of the metallic ions to the rare earth ions capable of emitting infrared radiation when excited with an exciting light source such that the pre-determined ratio corresponds to a parameter of a pre-selected decision criterion, wherein the parameter is chosen from emissions, magnetism, absorption, and decay times;
    c) at least one optical sensor arranged to detect, with spectral resolution, infrared radiation emitted from the luminescent compound excited by the exciting light source and to produce intensity data;
    d) at least one magnetic sensor arranged to detect the magnetic properties of the luminescent compound and to produce magnetic data; and
    e) a processing unit operating under a predefined program wherein the processing unit correlates the intensity data and the magnetic data for the value document, compares the intensity data with previously stored reference intensity data and the magnetic data with previously stored reference magnetic data, derives an authenticity indicator from the comparisons using the pre-selected decision criteria, and communicates the authenticity indicator thereby indicating authentication or lack of authentication of the value document.

2. The authentication system according to claim 1, wherein the host lattice comprises iron or chromium as absorptive elements.

3. The authentication system according to claim 1, wherein the host lattice has a garnet structure.

4. The authentication system according to claim 3, wherein the host lattice has a garnet structure described by the following general formula:

$$A_3B_{5-x}C_xO_{12}$$

where
   A stands for at least one ion from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, sodium and combinations thereof,
   B stands for at least one ion from the elements selected from the group consisting of iron, nickel, cobalt, chromium, manganese, vanadium and combinations thereof,
   C stands for at least one diamagnetic ion from the elements selected from the group consisting of aluminum, bismuth, gallium, scandium, chromium, titanium, germanium, vanadium, zinc, zirconium, magnesium, silicon and combinations thereof,
   x fulfills the condition $0 \leq x \leq 5$.

5. The authentication system according to claim 4, wherein the luminescent compound has the following general formula:

$$A_{3-y}RE_yB_{5-x}C_xO_{12}$$

where

A stands for at least one ion from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, and sodium combinations thereof, RE stands for at least one ion from the elements selected from the group consisting of praseodymium, neodymium, samarium, dysprosium, holmium, erbium, thulium, ytterbium, and combinations thereof, B stands for at least one ion from the elements selected from the group consisting of iron, nickel, cobalt, chromium, manganese, vanadium and combinations thereof, C stands for at least one diamagnetic ion from the elements selected from the group consisting of aluminum, bismuth, gallium, scandium, chromium, titanium, germanium, vanadium, zinc, zirconium, magnesium, silicon and combinations thereof, x fulfills the condition $0 \leq x < 5$, and y fulfills the condition $0.001 \leq y < 3$.

6. The authentication system according to claim 5, wherein A comprising at least two ions from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, and sodium.

7. The authentication system according to claim 5, wherein A comprising at least three ions from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, and sodium.

8. The authentication system according to claim 5, wherein A comprising at least four ions from the elements selected from the group consisting of yttrium, cerium, praseodymium, neodymium, samarium, europium, gadolinium, terbium, dysprosium, holmium, erbium, thulium, ytterbium, lutetium, lanthanum, indium, calcium, magnesium, and sodium.

9. The authentication system according to claim 5, wherein B comprising at least two ions from the elements selected from the group consisting of iron, nickel, cobalt, chromium, manganese, and vanadium.

10. The authentication system according to claim 5, wherein RE comprising at least two ions from the elements selected from the group consisting of praseodymium, neodymium, samarium, dysprosium, holmium, erbium, thulium, and ytterbium.

11. The authentication system according to claim 5, wherein C comprising at least two ions from the elements selected from the group consisting of aluminum, bismuth, gallium, scandium, chromium, titanium, germanium, vanadium, zinc, zirconium, magnesium, and silicon.

12. The authentication system according to claim 1, wherein the host lattice is ferromagnetic.

13. The authentication system according to claim 1, wherein the host lattice is ferrimagnetic.

14. The authentication system according to claim 1, wherein the host lattice is paramagnetic.

15. A method of securing a value document, comprising the step of:
pre-determining a ratio of metallic ions to rare earth ions capable of emitting infrared radiation when excited with an exciting light source such that the ratio corresponds to a parameter of a pre-selected authentication criteria, wherein the parameter is based on magnetism;
providing a luminescent compound comprising a host lattice having at least one metallic ion with magnetic properties and doped with at least one rare earth ion capable of emitting infrared radiation when excited with an exciting light source and having the ratio; and
adding the luminescent compound to the value document.

16. The method of claim 15, further comprising the steps of:
detecting magnetic data and intensity data from the luminescent compound,
correlating the intensity data and the magnetic data, and
comparing the intensity data with previously stored reference intensity data and the magnetic data with previously stored reference magnetic data.

17. The method of claim 16, further comprising the step of:
authenticating the value document based on the pre-selected authentication criteria.

18. The method of claim 15, wherein the host lattice includes iron, and wherein providing the luminescent compound comprising the host lattice having the ratio comprises altering the host lattice by exchanging some of the iron ions with ions chosen from aluminum, gallium, and/or scandium ions.

19. The method of claim 15, wherein the host lattice is YIG, and wherein providing the luminescent compound comprising the host lattice having the ratio comprises altering the host lattice by exchanging some of the yttrium ions with ions having unpaired electrons.

* * * * *